United States Patent [19]

Saito et al.

[11] Patent Number: 4,581,350
[45] Date of Patent: Apr. 8, 1986

[54] O-(PERFLUOROALKYLTHIOPHENYL) (THIO OR AMIDO) PHOSPHATES AS PESTICIDES

[75] Inventors: Junichi Saito, Tokyo; Akio Kudamatsu, Kanagawa; Toyohiko Kume; Shinichi Tsuboi, both of Tokyo, all of Japan

[73] Assignee: Nihon Tokushu Noyaku Seizo K.K., Tokyo, Japan

[21] Appl. No.: 612,094

[22] Filed: May 18, 1984

[30] Foreign Application Priority Data

May 27, 1983 [JP] Japan ................................ 58-92516

[51] Int. Cl.$^4$ ...................... A01N 57/02; C07F 9/105; C07F 9/201
[52] U.S. Cl. .................... 514/128; 558/196; 558/197; 558/195; 558/185; 558/99; 558/106; 558/87
[58] Field of Search .......................... 260/949; 514/128

[56] References Cited

U.S. PATENT DOCUMENTS 4,067,972  1/1978  Oswald et al. ...................... 260/949
4,139,615  2/1979  Hoffmann et al. .................. 260/949

FOREIGN PATENT DOCUMENTS 0097270  1/1984  European Pat. Off. .
2354336  1/1978  France .
2385726  10/1978  France .

Primary Examiner—Anton H. Sutto
Attorney, Agent, or Firm—Sprung Horn Kramer & Woods

[57] ABSTRACT

The invention relates to new organic phosphoric acid esters represented by the general formula

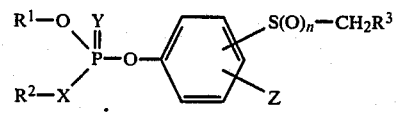

wherein
  X represents O, S or NH,
  Y represents O or S,
  $R^1$ represents a lower alkyl group,
  $R^2$ represents a lower alkyl group or a lower alkoxy-lower alkyl group,
  $R^3$ represents a fluoro-substituted lower alkyl group,
  Z represents a lower alkyl group, a lower alkoxy group or a halogen atom, and
  n represents 0 or 2,
which can be used as pesticidally active agents.

7 Claims, No Drawings

O-(PERFLUOROALKYLTHIOPHENYL) (THIO OR AMIDO) PHOSPHATES AS PESTICIDES

This invention relates to novel organic phosphoric acid esters, processes for their production, insecticidal, miticidal and nematocidal compositions containing these compounds and their use as pesticides.

More specifically, this invention relates to novel organic phosphoric acid esters represented by the following general formula (I)

$$R^1-O\underset{R^2-X}{\overset{O}{\diagdown}}P-O-\text{C}_6H_3(Z)-S(O)_n-CH_2R^3 \quad (I)$$

wherein·
X represents O, S or NH,
Y represents O or S,
$R^1$ represents a lower alkyl group,
$R^2$ represents a lower alkyl group or a lower alkoxy-lower alkyl group,
$R^3$ represents a fluoro-substituted lower alkyl group,
Z represents a lower alkyl group, a lower alkoxy group or a halogen atom, and
n represents 0 or 2.

The compounds of the general formula (I) can be produced by the following processes to which the invention also pertains.

(Process i)

A process for producing an organic phosphoric acid ester of general formula (I), which comprises reacting a phosphoric acid ester halide represented by the general formula $$R^1-O\underset{R^2-X}{\overset{Y}{\diagdown}}P-\text{Hal} \quad (II)$$

wherein X, Y, $R^1$ and $R^2$ are as defined, and Hal represents a halogen atom,
with a phenol represented by the general formula $$HO-\text{C}_6H_3(Z)-S(O)_n-CH_2R^3 \quad (III)$$

wherein $R^3$, Z and n are as defined, in the presence of a base.

(Process ii)

In the case of X=S:

A process for producing an organic phosphoric acid ester represented by the general formula $$R^1-O\underset{R^2-S}{\overset{Y}{\diagdown}}P-O-\text{C}_6H_3(Z)-S(O)_n-CH_2R^3 \quad (I\text{-}a)$$

wherein Y, $R^1$, $R^2$, $R^3$, Z and n are as defined above, which comprises reacting a phosphoric acid salt represented by the general formula $$R^1-O\underset{M^{\oplus}-S^{\ominus}}{\overset{Y}{\diagdown}}P-O-\text{C}_6H_3(Z)-S(O)_n-CH_2R^3 \quad (IV)$$

wherein Y, $R^1$, $R^3$, Z and n are as defined, and
M represents an alkali metal atom or an ammonium group,
with a halide represented by the general formula $$R^2-\text{Hal} \quad (V)$$

wherein $R^2$ and Hal are as defined.

Furthermore, the organic phosphoric acid ester of general formula (I) in accordance with this invention can be produced by the following process (iii). A compound of general formula (I) in which n is 2 can also be produced by the following process (iv).

(Process iii)

A process for producing the organic phosphoric acid ester of general formula (I) which comprises reacting a phosphoric acid ester halide represented by the general formula $$R^1-O\underset{\text{Hal}}{\overset{Y}{\diagdown}}P-O-\text{C}_6H_3(Z)-S(O)_n-CH_2R^3 \quad (VI)$$

wherein Y, $R^1$, $R^3$, Z, n and Hal are as defined, with a compound represented by the general formula $$R^2-X-H \quad (VII)$$

wherein X and $R^2$ are as defined.

(Process iv) (n=2)

A process for producing an organic phosphoric acid ester represented by the general formula $$R^1-O\underset{R^2-X}{\overset{Y}{\diagdown}}P-O-\text{C}_6H_3(Z)-SO_2-CH_2R^3 \quad (I\text{-}b)$$

wherein X, Y, $R^1$, $R^2$, $R^3$ and Z are as defined, which comprises reacting an organic phosphoric acid ester represented by the general formula $$R^1-O\underset{R^2-X}{\overset{Y}{\diagdown}}P-O-\text{C}_6H_3(Z)-S-CH_2R^3 \quad (I\text{-}c)$$

wherein X, Y, $R^1$, $R^2$, $R^3$ and Z are as defined, with a peroxide.

This invention also relates to arthropodicidal (insecticidal, miticidal) and nematocidal compositions containing organic phosphoric acid esters of the general formula (I).

U.S. Patent Specification No. 4,139,615 (corresponding to Japanese Laid-Open Patent Publication No.

151151/1977) a publication known before the filing of the present application, states to the effect that compounds of the general formula

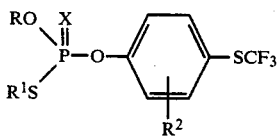

wherein R and $R^1$ are alkyl, $R^2$ is hydrogen or alkyl, and X is oxygen or sulfur,
have insecticidal, miticidal and nematocidal activities.

The present invention refers to new phosphoric acid esters of the general formula (I) which have unexpectedly excellent biological activities. Particularly the active compounds of formula (I) exhibit a very good control effect against noxious insects, mites and nematodes in agriculture, forestry and horticulture and animal husbandry.

It is an object of this invention therefore to provide the novel organic phosphoric acid esters of general formula (I), processes for production thereof, and their use as insecticidal, miticidal and nematocidal agents.

In the general formulae the lower alkyl groups $R^1$ and $R^2$ are the same or different and are straight-chain or branched alkyl having preferably 1 to 6, especially 1 to 4 carbon atoms. Methyl, ethyl, n- and iso-propyl, n-, iso-, sec.- and tert.-butyl may be mentioned as examples. Particularly preferred $R^1$ represents methyl or ethyl. Particularly preferred alkyl groups $R^2$ are methyl, ethyl, n- and iso-propyl and sec.-butyl.

In the lower alkoxy lower alkyl groups $R^2$ the alkyl parts may be the same or different and are straight-chain or branched and each have preferably 1 to 4, especially 1 or 2 carbon atoms. Methoxymethyl, ethoxyethyl, methoxyethyl and ethoxymethyl may be mentioned as examples for the lower alkyl groups $R^2$.

The lower alkyl and lower alkoxy groups Z are straight-chain or branched and have preferably 1 to 6, more preferred 1 to 4 and especially 1 or 2 carbon atoms. As examples methyl, ethyl, methoxy and ethoxy may be mentioned.

The fluoro substituted lower alkyl group $R^3$ may be straight-chain or branched and has preferably 1 to 6, more preferred 1 to 4 and especially 1 or 2 carbon atoms. These alkyl groups are preferably substituted by 1 to 5, more preferred by 1 to 4 and especially by 1 to 3 fluorine atoms. As particularly preferred groups $R^3$ the $CF_3$ group and the $CF_2CHF_2$ group may be mentioned. Most preferred is the $CF_3$ group.

Halogen Z means fluoro, chloro, bromo and iodo, preferably fluoro, chloro and bromo, more preferred chloro and bromo and especially chloro.

X represents O, S or NH, preferably O or S.
n represents O or 2, preferably O.

The group Z can be in all possible positions of the phenyl ring. Preferably it is in the 2- or 3-position (or 5- or 6-position respectively) and especially in the 3-position (or 5-position).

The $S(O)_n$—$CH_2$—$R^3$ group may be in all possible positions of the phenyl ring. Preferably it is in the 2-, 3- or 4-position (or 4-, 5- or 6-position respectively), especially it is in the 4-position of the phenyl ring.

Hal in general formulae II, V and VI means fluoro, chloro, bromo or iodo, preferably chloro or bromo and especially chloro.

M in formula IV means an alkali metal as sodium or potassium or an ammonium group which can be the unsubstituted ammonium group or organic ammonium groups such as lower alkyl ammonium groups (with preferably 1 to 4 carbon atoms per alkyl group) as e.g. trimethyl-ammonium or triethyl-ammonium.

Preferred are compounds of the general formula (I) in which
X represents O, S or NH,
Y represents O or S,
$R^1$ represents methyl or ethyl,
$R^2$ represents alkyl with 1 to 4 carbon atoms or alkoxyalkyl with 1 to 4 carbon atoms in each alkyl group,
$R^3$ represents $CF_3$ or $CF_2CHF_2$,
Z represents 3-methyl, 3-methoxy or 3-chloro,
n represents O or 2 and the $S(O)_n$—$CH_2R^3$ group is in the 4-position.

Most preferred are compounds of the general formula (I) in which
X represents O or S,
Y represents O or S,
$R^1$ represents methyl or ethyl,
$R^2$ represents methyl, ethyl, n- and i-propyl, sec.-butyl and ethoxyethyl,
$R^3$ represents $CF_3$ or $CF_2CHF_2$,
Z represents 3-methyl,
n represents O or 2 and the $S(O)_n$—$CH_2R^3$ group is in the 4-position.

The compound of general formula (I) in accordance with this invention can be produced by the following processes:

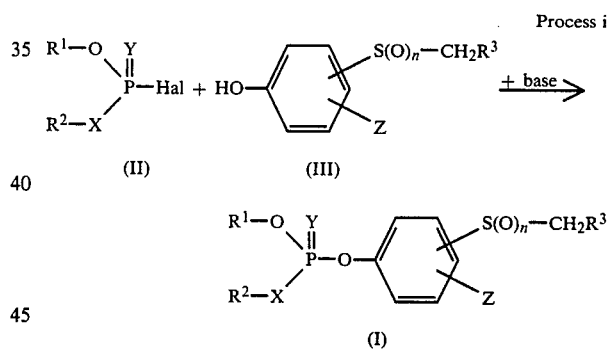

(In the above formulae, X, Y, $R^1$, $R^2$, $R^3$, Z and n are as defined above.)

In the process for producing the compound of this invention represented by the above reaction scheme, specific examples of the phosphoric acid ester halide of general formula (II) as a starting material include
O-ethyl-S-propyl-thiophosphoryl chloride,
O-ethyl-S-propyl-dithiophosphoryl chloride,
O,O-diethyl-thiophosphoryl chloride,
O,O-dimethyl-thiophosphoryl chloride,
O-ethyl-S-sec-butyl-thiophosphoryl chloride,
O-ethyl-S-ethoxyethylthiophosphoryl chloride,
O-ethyl-N-isopropylamidothiophosphoryl chloride, and
O-ethyl-N-isopropylamidophosphoryl chloride.

The corresponding bromides can also be cited.

Specific examples of the phenol of general formula (III) which is likewise a starting material include
3-methyl-4-(2,2,2-trifluoroethylthio)phenol,
3-methyl-2-(2,2,2-trifluoroethylthio)phenol,
3-methyl-4-(2,2,2-trifluoroethylsulfonyl)phenol, 3-methyl-4-(2,2,3,3-tetrafluoropropylthio)phenol,
3-methyl-2-(2,2,3,3-tetrafluoropropylthio)phenol,
3-methyl-4-(2,2,3,3,3-pentafluoropropylthio)phenol,
3-methyl-4-(2,2,3,3-tetrafluoropropylsulfonyl)phenol,
3-methoxy-4-(2,2,2-trifluoroethylthio)phenol, and
3-chloro-4-(2,2,2-trifluoroethylthio)phenol.

Specific examples of the base used in the above reaction scheme include inorganic bases such as sodium hydroxide, potassium hydroxide, potassium carbonate and sodium carbonate and organic bases such as triethylamine, pyridine, N,N-dimethylaniline and isopropylamine.

By citing a typical example, the above manufacturing process will be specifically described.

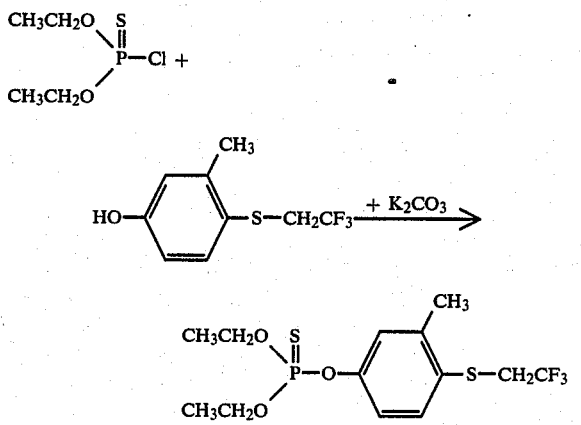

The process for producing the active compound of this invention can be carried out desirably by using a solvent or diluent. For this purpose all inert solvents and diluents can be used.

Examples of such solvents or diluents include water; aliphatic, alicyclic and aromatic hydrocarbons (which may optionally be chlorinated) such as hexane, cyclohexane, petroleum ether, ligron, benzene, toluene, xylene, methylene chloride, chloroform, carbon tetrachloride, ethylene chloride, trichloroethylene and chlorobenzene; ethers such as diethyl ether, methyl ethyl ether, diisopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; tertiary alcohols such as tert-butyl alcohol; esters such as ethyl acetate and amyl acetate; acid amides such as dimethylformamide and dimethylacetamide; sulfones and sulfoxides such as dimethyl sulfoxide and sulfolane; and bases such as pyridine.

As already mentioned, the reaction in accordance with this invention may be carried out in the presence of an acid binder. Examples of the acid binder are hydroxides, carbonates and alcoholates of alkali metals, and tertiary amines (e.g., triethylamine, diethylaniline, dimethylaniline and pyridine) which are normally used.

The process of this invention can be performed within a broad temperature range. For example, it can be carried out at a temperature between about 0° and about 150° C., preferably between about 10° and about 70° C. Desirably, the reaction is carried out under atmospheric pressure, but it is possible to operate under elevated or reduced pressure.

By the process (i) described above, the final product of this invention having a high purity can be obtained in high yields.

The compounds of this invention can alternatively be produced by the following processes (ii), (iii) and (iv).

In the case of X = S:  Process ii

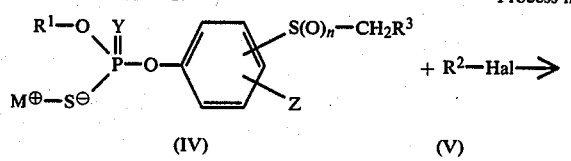

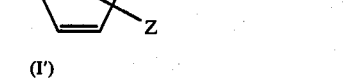

(In the formulae, Y, $R^1$, $R^2$, $R^3$, Z, n, Hal and M are as defined hereinabove.)

Process iii

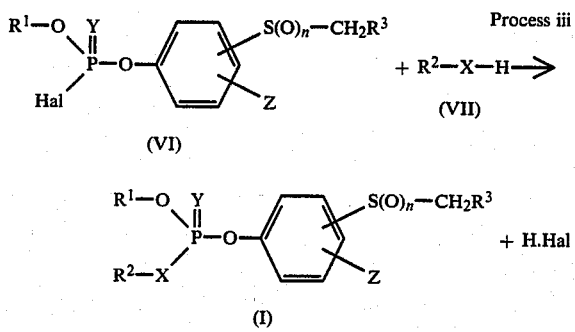

In the case of n = 2:  Process iv

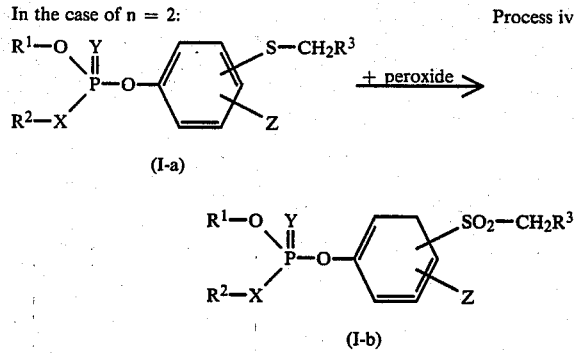

(In the above formulae, X, Y, $R^1$, $R^2$, $R^3$ and Z are as defined hereinabove.)

The following Referential Examples are given for the processes (ii), (iii) and (iv) above.

(Process ii)—Referential Example—

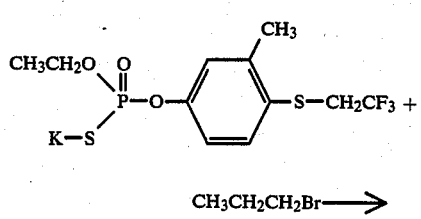

-continued

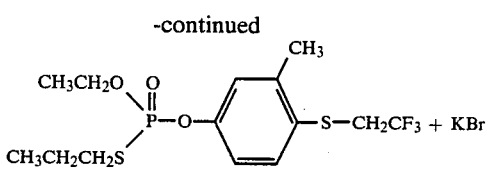

The above process can be easily practiced under the same reaction conditions using the same inert solvent or diluent as exemplified with regard to process (i).

(Process iii)—Referential Example—

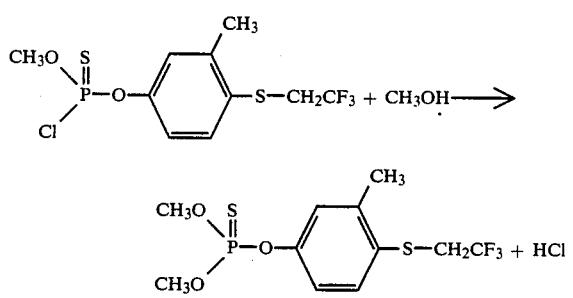

The above process can be easily practiced under the same reaction conditions using the same inert solvent or diluent as exemplified with regard to process (i) excepting water and alcohols.

(Process iv)—Referential Example—

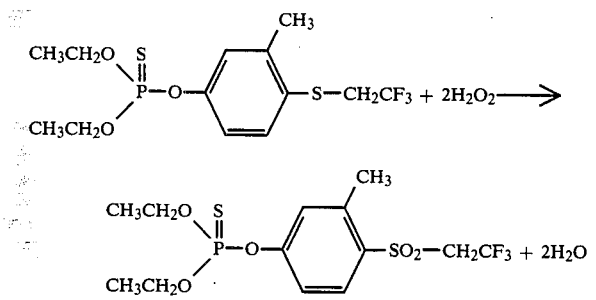

In the above reaction scheme, m-chloroperbenzoic acid, etc. may be used instead of hydrogen peroxide.

The above process can be easily practiced under the same reaction condition using the same inert solvent or diluent as exemplified with regard to process (i).

The active compounds of this invention exhibit an accurate control effect against noxious insects, mites and nematodes without causing phytotoxicity to cultivated plants. The compounds of this invention can be applied to the control and eradication of a wide range of pests, noxious sucking and biting insects, other plant parasites, pests on stored grains, and pests detrimental to hygiene.

Examples of such pests are shown below.

Examples of insects include coleopterous insects such as *Callosobruchus chinensis, Sitophilus Zeamais, Tribolium castaneum, Epilachna vigintioctomaculata, Agriotes fuscicollis, Anomala rufocuprea, Leptinotarsa decemlineata, Diabrotica spp., Monochamus alternatus,* and *Lyctus brunneus;* lepidopterous insects such as *Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Galleria mellonella* and *Phyllocnistis citrella;* hemipterous insects such as *Nephotettix cincticeps, Nilaparvata lugens, Pseudococcus comstocki, Unaspis Yanonensis, Myzus persicae, Aphis pomi, Rhopalosiphum pseudobrassicas, Stephanitis nashi, Nazara spp., Cimex lectularius, Trialeurodes vaporariorum* and *Psylla* spp.; orthopterous insects such as *Blatella germanica, Periplaneta americana, Gryllotalpa africana* and *Locusta migratoria migratoriodes;* isopterous insects such as *Deucotermes speratus* and *Coptotermes formosanus;* and dipterous insects such as *Musca domestica, Aedes aegypti, Hylemia platura, Culex pipiens, Anopheles sinensis* and *Culex tritaeniorhynchus.*

Examples of mites are *Tetranychus telarius, Panonychus citri, Aculus pelekassi* and *Torronomus* spp.

Examples of the nematodes are *Meloidogyne incognita, Bursaphelenchus lignicolus* Mamiya et Kiyohara, *Aphelenchoides besseyi, Heterodera glycines* and *Pratylenchus* spp.

In the field of animal husbandry, the novel compounds of this invention can be effectively used against various animal parasites, such as mites (including ticks), insects and worms. Examples of such animal parasites include such mites as *Oranithodoros* spp., *Ixodes* spp., and *Boophilus* spp., and such insects as *Gastrophilus* spp., *Stomoxys* spp., *Trichodectes* spp., *Rhodnius* spp., and *Ctenocephalides canis.*

In the present invention, substances which have a controlling effect against these pests are sometimes referred to generically as pesticides.

For use as an insecticidal, miticidal and nematocidal agent, the active compound of this invention may be diluted directly with water, or formulated into various forms using agriculturally acceptable adjuvants by methods generally practiced in the production of agricultural chemicals. In actual use, these various formulations may be applied directly or after diluting them with water to the desired concentrations.

Examples of the agriculturally acceptable adjuvants are diluents (solvents, extenders, carriers), surface-active agents (solubilizing agents, emulsifiers, dispersants, wetting agents), stabilizers, stickers, aerosol propellants and synergists.

Examples of the solvents are water, and organic solvents, for example hydrocarbons (e.g., n-hexane, petroleum ether, naphtha, petroleum fractions (e.g., paraffin waxes, kerosene, light oils, middle oils, and heavy oils), benzene, toluene, and xylenes), halogenated hydrocarbons (e.g., methylene chloride, carbon tetrachloride, trichloroethylene, ethylene chloride, ethylene dibromide, chlorobenzene and chloroform), alcohols (e.g., methyl alcohol, ethyl alcohol, propyl alcohol, and ethylene glycol), ethers (e.g., ethyl ether, ethylene oxide and dioxane), alcohol ethers (e.g., ethylene glycol monomethyl ether), ketones (e.g., acetone and isophorone), esters (e.g., ethyl acetate and amyl acetate), amides (e.g., dimethylformamide and dimethylacetamide) and sulfoxides (e.g., dimethyl sulfoxide).

Examples of the extenders or carriers include inorganic powders, for example slaked lime, magnesium lime, gypsum, calcium carbonate, silica, perlite, pumice, calcite, diatomaceous earth, amorphous silica, alumina, zeolites, and clay minerals (e.g., pyrophyllite, talc, montmorillonite, beidellite, vermiculite, kaolinite and mica); vegetable powders such as cereal powders, starches, processed starches, sugar, glucose and crushed stalks of plants; and powders of synthetic resins such as phenolic resins, urea resins, and vinyl chloride resins.

Examples of the surface-active agents include anionic surface-active agents such as alkylsulfuric acid esters (e.g., sodium laurylsulfate), arylsulfonic acids (e.g., alkylarylsulfonic acid salts and sodium alkylnaphthalenesulfonates), succinic acid salts, and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chloride) and polyoxyethylene alkylamines; nonionic surface-active agents such as polyoxyethylene glycol ethers (e.g., polyoxyethylene alkylaryl ethers and the condensation products thereof), polyoxyethylene glycol esters (e.g., polyoxyethylene fatty acid esters), and polyhydric alcohol esters (e.g., polyoxyethylene sorbitan monolaurate); and amphoteric surface-active agents.

Examples of other adjuvants include stabilizers; stickers (e.g., agricultural soaps, casein lime, sodium alginate, polyvinyl alcohol, vinyl acetate-type adhesives and acrylic adhesives; aerosol propellants (e.g., trichlorofluoromethane, dichlorofluoromethane, 1,2,2-trichloro-1,1,2-trifluoroethane, chlorobenzene, LNG, and lower ethers); combustion controlling agents for fumigants (e.g., nitrite salts, zinc powder, dicyandiamide); oxygen yielding agents (e.g., chlorate salts, bichromate salts); dispersion stabilizers (e.g., casein, tragacanth, carboxymethyl cellulose (CMC) and polyvinyl alcohol (PVA); and synergists.

The compounds of this invention can be formed into various formulations by methods generally practiced in the production of agricultural chemicals. Examples of the formulations are emulsifiable concentrates, oils, wettable powders, soluble powders, suspensions, dusts, granules, pulverulent compositions, fumigants, tablets, pastes and capsules.

The insecticidal, miticidal and nematocidal agents of this invention may contain about 0.1 to about 95% by weight, preferably about 0.5 to about 10% by weight, of the aforesaid active ingredient.

In actual use, the suitable amount of the active compound in the aforesaid formulations and ready-to-use preparations is, for example, about 0.0001 to about 20% by weight, preferably about 0.005 to about 10% by weight.

The content of the active ingredient can be properly varied depending upon the type of the formulation, the method, purpose, time and locus of its application, the state of occurrence of pests to be controlled, etc.

If required, the compound of this invention may be used further in combination with other agricultural chemicals, for example other insecticides, fungicides, other miticides, other nematocides, antiviral agents, herbicides, plant growth regulators and attractants [e.g., organophosphate compounds, carbamate compounds, dithio(or thiol)carbamate compounds, oranochlorine compounds, dinitro compounds, organosulfur or organometallic compounds, antibiotics, substituted diphenyl ether compounds, urea compounds, and triazine compounds], and/or fertilizers.

Various compositions and ready-to-use preparations containing the aforesaid active ingredient can be applied by various methods generally practiced in the field of agricultural chemical application, for example spraying (e.g., liquid spraying, misting, atomizing, dusting, granule scattering, water surface application, and pouring); fumigation; soil application (e.g., mixing, sprinkling, vaporing, pouring); surface application (e.g., coating, banding, dust coating, covering); and dipping. They can also be used by the so-called ultralow volume spraying method. According to this method, the active ingredient may be included in a concentration of 100%.

The rate of application per unit area is, for example, about 0.03 to about 10 kg, preferably about 0.3 to about 6 kg, per hectare. In special cases, however, it may be, and sometimes should, be outside the specified range.

According to this invention, there can be provided an insecticidal, miticidal and nematocidal composition comprising the compound of general formula (I) as an active ingredient and a diluent (a solvent and/or an extender and/or a carrier) and/or a surface-active agent, and if further required, a stabilizer, a sticker, a synergist, etc.

This invention also provides a method for controlling insects, mites and nematodes, which comprises applying to insects, mites and nematodes and/or their habitat the compound of general formula (I) alone or in admixture with a diluent (a solvent and/or an extender and/or a carrier) and/or a surface-active agent and if further required, a stabilizer, a sticker, a synergist, etc.

The following examples illustrate the present invention specifically. It should be noted however that the invention is not limited to these specific examples alone.

EXAMPLE 1

(Compound No. 1)

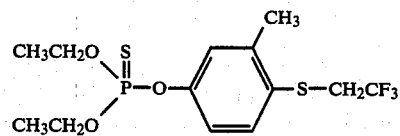

At 20° to 30° C., 23.6 g of O,O-diethyl-thiophosphoryl chloride was added dropwise to a mixture composed of 30 g of 3-methyl-4-(2,2,2-trifluoroethylthio)phenol, 19 g of anhydrous potassium carbonate and 200 ml of methyl isobutyl ketone. The reaction mixture was stirred continuously at 55° to 60° C. for 6 hours, cooled, and washed successively with water, a 1% aqueous solution of sodium hydroxide, and water in this order. The purified organic layer was dried over anhydrous sodium sulfate, and low-boiling substances were evaporated under reduced pressure to give 43.6 g of the desired O,O-diethyl O-[3-methyl-4-(2,2,2-trifluoroethylthio)phenyl]thiophosphate. $n_D^{20} = 1.5076$.

By substantially the same procedure as above, O,O-dimethyl O-[3-methyl-4-(2,2,2-trifluoroethylthio)phenyl]thiophosphate ($n_D^{20} = 1.5202$) of the following formula (Compound No. 2)

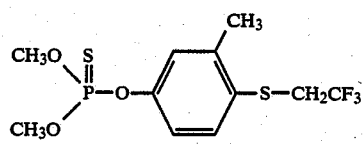

was synthesized. The compounds shown in Table 1 below were also synthesized by substantially the same procedure as above.

TABLE 1

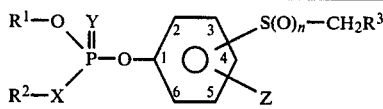

| Compound No. | X | Y | R¹ | R² | Z | $S(O)_n$—$CH_2R^3$ | Refractive index $n_D^{20}$ |
|---|---|---|---|---|---|---|---|
| 3 | S | O | —$C_2H_5$ | n-$C_3H_7$ | 3-$CH_3$ | 4-S—$CH_2CF_2CHF_2$ | |
| 4 | S | O | —$C_2H_5$ | n-$C_3H_7$ | 3-$CH_3$ | 4-S—$CH_2CF_3$ | 1.5705 |
| 5 | S | O | —$C_2H_5$ | n-$C_3H_7$ | 3-$CH_3$ | 6-S—$CH_2CF_3$ | |
| 6 | S | S | —$C_2H_5$ | n-$C_3H_7$ | 3-$CH_3$ | 4-S—$CH_2CF_3$ | 1.5400 |
| 7 | O | S | —$C_2H_5$ | —$C_2H_5$ | 3-$CH_3$ | 4-$S(O)_2$—$CH_2CF_3$ | |
| 8 | S | O | —$C_2H_5$ | sec-$C_4H_9$ | 3-$CH_3$ | 4-S—$CH_2CF_3$ | |
| 9 | S | O | —$C_2H_5$ | —$C_2H_4OC_2H_5$ | 3-$CH_3$ | 4-S—$CH_2CF_3$ | |
| 10 | NH | S | —$C_2H_5$ | iso-$C_3H_7$ | 3-$CH_3$ | 4-S—$CH_2CF_3$ | |
| 11 | S | S | —$C_2H_5$ | n-$C_3H_7$ | 3-Cl | 4-S—$CH_2CF_3$ | |
| 12 | S | O | —$C_2H_5$ | n-$C_3H_7$ | 3-$OCH_3$ | 4-S—$CH_2CF_3$ | |
| 13 | NH | O | —$C_2H_5$ | iso-$C_3H_7$ | 3-$CH_3$ | 4-S—$CH_2CF_3$ | 1.4907 |

It was ascertained that the compounds indicated in Table 1 can be easily produced by process (i). Other compounds of this invention than those exemplified above can be easily produced by substantially the same process as above. The respective compounds can also be produced according to processes (ii) to (iv).

EXAMPLE 2

Wettable powder:

Fifteen parts of compound No. 1 of the invention, 80 parts of a 1:5 mixture of white carbon (fine powder of hydrous amorphous silicon dioxide) and powdery clay, 2 parts of sodium alkylbenzenesulfonate, and 3 parts of a sodium alkylnaphthalenesulfonate/formaldehyde condensate are pulverized and mixed to form a wettable powder. It is diluted with water and sprayed onto insects, mites and nematodes and/or their habitat.

EXAMPLE 3

Emulsifiable concentrate:

Thirty parts of compound No. 2 of the invention, 55 parts of xylene, 8 parts of polyoxyethylene alkyl phenyl ether and 7 parts of calcium alkylbenzenesulfonate are mixed with stirring to form an emulsifiable concentrate. It is diluted with water and sprayed onto insects, mites and nematodes and/or their habitat.

EXAMPLE 4

Dust:

Two parts of compound No. 3 of the invention and 98 parts of powdery clay are pulverized and mixed to form a dust. It is scattered over insects, mites and nematodes and/or their habitat.

EXAMPLE 5

Dust:

Compound No. 4 of the invention (1.5 parts), 0.5 part of isopropyl hydrogen phosphate, and 98 parts of powdery clay are pulverized and mixed to form a dust. It is scattered over insects, mites and nematodes and/or their habitat.

EXAMPLE 6

Granules:

Water (25 parts) is added to a mixture consisting of 10 parts of compound No. 5 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over insects, mites and nematodes and/or their habitat.

EXAMPLE 7

Granules:

Ninety-five parts of clay mineral particles having a particle size distribution between 0.2 and 2 mm are put in a rotary mixer, and with rotation, 5 parts of compound No. 6 of the invention is sprayed onto the particles to wet them uniformly. The granules obtained are scattered over insects, mites and nematodes and/or their habitat.

EXAMPLE 8

Oil:

Compound No. 7 of the invention (0.5 part) and 99.5 parts of kerosene are mixed with stirring to form an oil. It is sprayed onto insects, mites and nematodes and/or their habitat.

EXAMPLE 9

Test on *Callosobruchus chinensis:*

Preparation of a test chemical

Solvent: 3 parts by weight of xylene

Emulsifier: 1 part by weight of polyoxyethylene alkylphenyl ether

To form a preparation of a suitable active compound, 1 part by weight of the active compound was mixed with the aforesaid amount of the solvent containing the aforesaid amount of the emulsifier, and the mixture was diluted with water to a prredetermined concentration.

Testing method

A filter paper was spread on a Petri dish having a diameter of 9 cm, and 1 ml of a water dilution of the active compound in a predetermined concentration was put in it. Twenty heads of *Callosobruchus chinensis* were released into the Petri dish, and the dish was placed in a chamber kept at 28° C. The number of dead insects was examined 24 hours later, and the kill ratio was calculated.

The results are shown in Table 2.

TABLE 2

| Compound No. | Concentration of the active ingredient (ppm) | Kill ratio (%) |
| --- | --- | --- |
| 1 | 1 | 100 |
| 2 | 1 | 100 |
| 3 | 1 | 100 |
| 4 | 1 | 100 |
| Comparison A-1 | 10 | 60 |
|  | 1 | 0 |

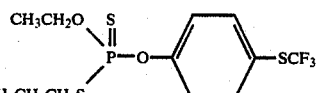

Note: Comparison A-1 CH$_3$CH$_2$CH$_2$S (Compound described in U.S. Pat. No. 4,139,615)

EXAMPLE 10

Test on *Tetranychus telarius* (spray test):

Fifty to one hundred imagoes of *Tetranychus telarius* having resistance to organophosphorus agents were inoculated on the leaves of garden pea in the stage where two main leaves developed, which was cultivated in pots having a diameter of 6 cm. Two days later, a water dilution in a predetermined concentration of the active compound prepared as in Example 9 was sprayed at a rate of 40 ml per pot. The pots were placed in a greenhouse, and the control effect was evaluated 10 days later by the following control indices.

3: The number of surviving imagoes was 0%.
2: The number of surviving imagoes was more than 0% but less than 5% of that in a non-treated area.
1: The number of surviving imagoes was 5 to 50% of that in the non-treated area.
0: The number of surviving imagoes exceeded 50% of that in the non-treated area.

The results are shown in Table 3.

TABLE 3

| Compound No. | Concentration of the active ingredient (ppm) | Control index |
| --- | --- | --- |
| 1 | 100 | 3 |
| 2 | 100 | 3 |
| 9 | 100 | 3 |
| Comparison A-1 | 100 | 0 |

Note:
Comparison A-1 is the same as in Table 2.

EXAMPLE 11

Test on German cockroach (*Blatella germanica*):
Testing method

A filter paper was spread on a Petri dish having a diameter of 9 cm, and 1 ml of a water dilution in a predetermined concentration of the active compound prepared as in Example 9 was put into it. Ten imagoes of German cockroach were released into the Petri dish, and the Petri dish was placed in a chamber kept at 28° C. Twenty four hours later, the number of dead insects was examined, and the kill ratio was calculated.

The results are shown in Table 4.

TABLE 4

| Compound No. | Concentration of the active ingredient (ppm) | Kill ratio (%) |
| --- | --- | --- |
| 1 | 10 | 100 |
| 2 | 10 | 100 |
| 3 | 100 | 100 |
| 4 | 10 | 100 |
| 5 | 100 | 100 |
| 6 | 100 | 100 |
| 7 | 100 | 100 |
| 8 | 100 | 100 |
| Compound A-1 | 100 | 10 |

Note:
Comparison A-1 is the same as in Table 2.

EXAMPLE 14

Test on larvae of *Culex pipiens*:
Testing method

One hundred milliliters of a water dilution in a predetermined concentration of the active compound prepared as in Example 9 was placed in a tall Petri dish having a diameter of 9 cm, and 25 fourth-instar larvae of *Culex pipiens* were released into it, and the Petri dish was placed in a chamber kept at 28° C. The number of dead insects was examined 24 hours later and the kill ratio was calculated.

The results are shown in Table 5.

TABLE 5

| Compound No. | Concentration of the active ingredient (ppm) | Kill ratio (%) |
| --- | --- | --- |
| 2 | 0.01 | 100 |
| Comparison A-1 | 0.1 | 70 |
|  | 0.01 | 0 |

Note:
Comparison A-1 is the same as in Table 2.

EXAMPLE 13

Test on *Meloidogyne incognita*:
Preparation of a test chemical

Two parts of the active compound and 98 parts of talc were pulverized and mixed.

Testing method

The test chemical prepared as above was added in a dosage of 25 and 10 ppm, respectively, to soil contaminated with *Meloidogyne incognita*. They were uniformly mixed with agitation, and the mixture was filled in pots (1/5000 are). Seeds of tomato (variety: Kurihara) were sown therein at a rate of about 20 per pot. The tomatoes were then cultivated in a greenhouse. Four weeks later, the plants were pulled up with a care taken not to damage their roots. The degree of damage was examined on 10 of the pulled plants.

The results of the test shown that the compounds of this invention, for example compounds Nos. 10 and 13 produced a control effect of almost 100% when applied in 10 to 25 ppm as the concentration of the active ingredient.

It will be appreciated that the instant specification and examples are set forth by way of illustration and not limitation, and that various modifications and changes may be made without departing from the spirit and scope of the present invention.

What is claimed is:

1. An organic phosphoric acid ester of the formula

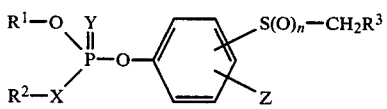

wherein
X represents O, S or NH,
Y represents O or S,
R¹ represents methyl or ethyl,
R² represents a lower alkyl group or a lower alkoxy-lower alkyl group with 1 to 4 carbon atoms in each alkyl group,
R³ represents $CF_3$ or $CF_2CHF_2$,
Z represents 3-methyl, 3-methoxy or 3-chloro,
n represents 0 or 2, and the $S(O)_n$—$CH_2R^3$ group is in the 4-position.

2. A method of combatting insects, mites and nematodes which comprises applying to such insects, mites and nematodes or to a habitat thereof an insecticidally, miticidally and nematocidally effective amount of a compound according to claim 1.

3. The method according to claim 2, wherein such compound is
O,O-dimethyl O-[3-methyl-4-(2,2,2-trifluoroethylthio)-phenyl]thiophosphate or
O,O-diethyl O-[3-methyl-4-(2,2,2-trifluoroethylthio)-phenyl]thiophosphate.

4. An organic phosphoric acid ester according to claim 1,
in which
X represents O or S,
Y represents O or S,
R¹ represents methyl or ethyl,
R² represents methyl, ethyl, n- and i-propyl, sec.-butyl and ethoxyethyl,
R³ represents $CF_3$ or $CF_2CHF_2$,
Z represents 3-methyl,
n represents 0 or 2 and the $S(O)_n$—$CH_2R^3$ group is in the 4-position.

5. A compound according to claim 1, wherein such compound is O,O-dimethyl O-[3-methyl-4-(2,2,2-trifluoroethylthio)phenyl]thiophosphate of the formula

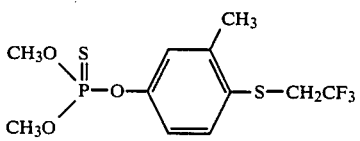

6. A compound according to claim 1, wherein such compound is O,O-diethyl O-[3-methyl-4-(2,2,2-trifluoroethylthio)phenyl]thiophosphate of the formula

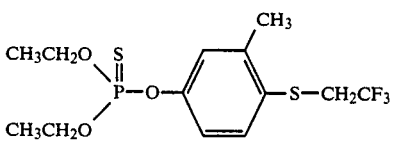

7. An insecticidal, miticidal and nematocidal composition comprising an insecticidally, miticidally and nematocidally effective amount of a compound according to claim 1 in admixture with a diluent.

* * * * *

UNITED STATES PATENT AND TRADEMARK OFFICE
CERTIFICATE OF CORRECTION

PATENT NO. : 4,581,350
DATED : April 8, 1986
INVENTOR(S) : Junichi Saito, et al.

It is certified that error appears in the above-identified patent and that said Letters Patent is hereby corrected as shown below:

Col. 1, line 15    Middle of formula delete "$\overset{O}{\underset{\|}{}}$" and substitute: $\overset{>P}{\underset{\underset{>P}{\overset{\|}{Y}}}{}}$ Col. 6, line 50    Delete right side of formula and substitute 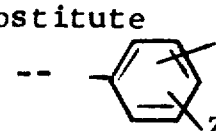

Col. 9, line 58    Correct spelling of "organochlorine"
Col. 12, line 57   Correct spelling of "predetermined"

Signed and Sealed this

Fifteenth Day of July 1986

[SEAL]

Attest:

DONALD J. QUIGG

Attesting Officer    Commissioner of Patents and Trademarks